United States Patent [19]

Davis et al.

[11] Patent Number: 4,561,983

[45] Date of Patent: Dec. 31, 1985

[54] METHOD FOR CONTROLLING MOLLUSKS

[75] Inventors: Dwight P. Davis, Newtown, Pa.;
Francis G. Doherty, Blacksburg, Va.

[73] Assignee: Betz Laboratories, Inc., Trevose, Pa.

[21] Appl. No.: 638,595

[22] Filed: Aug. 7, 1984

[51] Int. Cl.$^4$ ............................................... C02F 1/50
[52] U.S. Cl. .................................................. 210/755
[58] Field of Search ...................... 210/755, 764, 749

[56] References Cited

U.S. PATENT DOCUMENTS 3,524,812  8/1970  Shema et al.
3,871,860  3/1975  Marowitz et al. .............. 210/755 X
4,462,914  7/1984  Smith ................................. 210/755

OTHER PUBLICATIONS

"Clams-A Growing Threat To Inplant Water Systems", Plant Engineering, Jun. 1979.
Preamble to Steam Electric Power Generating Point Source Category Effluent Limitation Guidelines (47FR52290).
"Corbicula Variation and Dreissena Parallels", The Biologist, vol. 53, No. 3, Aug. 1971, pp. 153–159.
"Thermal Tolerance of the Adult Asiatic Clam *Corbicula Manilensis*", Mattice and Dye, Proceedings of Second Thermal Ecology Symposium, Apr. 1975.
"Procedures for Evaluating Chemical Control of Larval Asiatic Clams", Foster and Box.
Untitled paper (18 pages) on "Asiatic Clams . . . " with bibliography.

*Primary Examiner*—Thomas Wyse
*Attorney, Agent, or Firm*—Alexander D. Ricci; Bruce E. Peacock; James D. Dee

[57] ABSTRACT

To control the fouling potential of mollusks in aqueous systems, an effective amount for the purpose of an effective nitrostyrene compound is added to said systems.

14 Claims, No Drawings

METHOD FOR CONTROLLING MOLLUSKS

BACKGROUND OF THE INVENTION

As indicated in the article entitled "Clams—A Growing Threat To Inplant Water Systems" *Plant Engineering,* June, 1979, page 165 et seq., Corbicula ssp, the so called asiatic clam, has become and currently is a major problem in industrial plants and utility systems which utilize large quantities of water particularly for cooling water and more particularly in once-through cooling water systems.

For further information see also Mattice, J. S.,1979. "Interactions of Corbicula ssp, with power plants," pages 119-138 and Goss, L. B. et al, 1979. "Control Studies on Corbicula for steam electric generating plants," pages 139-151. In J. C. Britton (ed) Proceedings, First International Corbicula Symposium, Texas Christian University Research Foundation, Fort Worth, Tex., 313 pages.

Cooling systems which use cooling water on a one-time basis before discharging it directly to waste are termed oncethrough cooling systems. Since even small cooling systems operating on a once-through basis use relatively large amounts of cooling water, these systems are generally employed only where water at a suitably low temperature is readily available in large volumes and at low costs.

The usual source of once-through cooling water is from wells, rivers and lakes where the only cost involved is that of pumping. Generally, the only external treatment applied to once-through waters taken from rivers and lakes is screening to remove objects which are large enough that they could damage pumps and heat exchanger equipment.

Asiatic clams (Corbicula spp) were first discovered in the United States in 1938 in the Columbia River in Washington. Since then the range of this exotic species has widely expanded and presently it is found in at least thirty-three states. The spread of this species has been of special interest because of problems it has caused in the water supply systems in electric power plants, industrial plants and municipalities.

As indicated in the above identified article from *Plant Engineering:*

"Infestation is usually limited to that part of an industrial plant or operation that uses fresh, untreated lake or river water. The majority of problems result from plugging by clam shells. Adult shell-bearing clams may be drawn into a plant's water system and carried to a condenser, where they can plug the tubes. In most cases, the organisms enter the system in the larval stage and develop to maturity in areas of low water velocity. When the clams die, their shells may be carried by the water to areas susceptible to plugging. These can include cooling systems for compressors, condensers, blast furnaces, and other processes.

Live clams have also been found in the media of raw-water pressure filters, upstream of softeners, and in solids depositions in water basins. Normally, cooling-tower water systems are free of the organisms, because such systems have relatively high-temperature water and receive biocide treatment.

One-year-old clams are capable of plugging valves and nozzles. Two-year-old clams can cause mechanical damage to impellers and other moving parts of water-distribution systems. At six years, the clam can damage tires of construction vehicles. As in all other clams, growth is rapid in early years and then tapers off."

The clams are very tolerant of many chemicals and often occur in great abundance. They have accumulated to depths of two meters in the Delta-Mendota Canal in California and have caused reductions in water flow. Some industrial plants have had difficulty obtaining fire insurance after inspectors found the fire protection systems plugged with Corbicula shells. Pump impellers have been damaged by shells in some industrial plants. The number of power plants which have experienced problems with this species has increased during the past several years. Problems in fossil-fueled power plants most often relate to pluggage of condenser tubes, surface water heat exchangers, and blockage of fire protection systems. In addition to these problems nuclear power plants may have other problems associated with the shutdown service water, and emergency reactor cooling systems. In April of 1981 the Nuclear Regulatory Commission issued the Inspection and Enforcement Bulletin #81-03 concerning the flow blockage of cooling water to safety system components by Corbicula.

An examination of the biology of the Corbicula provides some explanation of how this organism is able to cause such serious problems in water supply systems. The Asiatic clams have a strong, thick shell which is almost spherical in shape. They normally obtain a shell length of 20-40 mm (depending on the environment) but become sexually mature at only 10 mm. Corbicula are hermaphroditic so every mature clam produces eggs which are incubated in the gills and released as a larval form called a veliger. They may spawn continually at water temperature above 16° C. (60° F.). Published information indicates that during the spring and fall spawning peaks each clam may release as many as 588 veligers per day. When one considers that adult Corbicula can attain a density of 20,000/m$^2$, it follows that several million veligers could be released from each square meter per day. The diameter of the veliger when it is released is about 200 microns (0.008 inches) and it is a weak swimmer usually found near the bottom of the water column. The small size and tremendous number of veligers explains how they can so successfully gain entrance to untreated water systems. If conditions are favorable, these veligers can develop into clams with a shell length of 10-15 mm (depending on the environment) within a year and create problems in water lines. The adult clams are very tolerant of many chemicals and their thick shells can cause problems even after the clams have died.

The differences in size and chemical tolerances of the various life stages of Asiatic clams have complicated attempts to control them. Controls are also complicated by the different types of problems that clams have caused in various water systems. Because of these complexities, it appears that a single control measure has not previously been effective for all life stages or all water systems and control methods have had to be specific in their application. A variety of control measures have been studied for use in power plants and one of the most effective controls is one which is designed for static water systems such as fire protection systems, and consists of a 0.8 mm (1/32 inch) filter screen and chlorine injection. Chlorine at 0.5 ppm for 72 hours will result in 100% mortality of the veligers. This method offers probably the best control but presents environmental and regulatory problems. Regulations limiting the discharge of chlorine would prohibit its use, although variances are sometimes granted.

According to the Plant Engineering article:

> Primary considerations in selecting a plant control procedure for Corbicula larvae are the compatibility of the method with the water system, the ability to meet effluent and stream water-quality standards if a chemical control agent is used, and economics. Because the clams cannot live in temperatures above 78° F. (26° C.), heating can provide effective control. However, this method is not applicable to all water systems. In some systems, the water volume that must be heated is too large or the system's design will not allow the heated water to reach all areas suitable for clam propagation.
>
> Control with chlorine is somewhat limited because it is difficult to maintain the necessary chlorine concentrations in static water lines.
>
> Mechanical devices, such as traps, can be used to prevent mature clams from entering water systems and for removing clams or shells from systems. Screens and traps may not be effective in preventing clam larvae infestation, but they often are used as an integral part of a general biological control program.
>
> The organism must be controlled in the freefloating or juvenile stages to prevent the development of problem-causing mature, shell-bearing clams.

DESCRIPTION OF THE INVENTION

The present inventors discovered that the survival of veliger stage mollusks in a laboratory test system could be significantly impaired by adding to the system a sufficient amount for the purpose (depending upon the severity or potential severity of the problem) of an effective nitrostyrene compound. The treatment may range from about 0.1 to 1000 parts of compound to a million parts of the aqueous system to be treated (ppm). Veliger stage mollusks which are particularly affected by the compound are the asiatic clams, more specifically Corbicula spp.

The nitrostyrene compound which has been found to be effective is the bromonitrostyrene and in particular beta-bromo-beta nitrostyrene.

For example, it is believed that adding the nitrostyrene compound in an effective amount to the incoming water of a once-through cooling system to destroy the planktonic juveniles before such settle and form the adult clam or mollusks, does provide quite adequate inhibition of clam infestation and the consequent encrustation of the structural parts of the cooling water system. Treatment after formation of the adult mollusks is not as satisfactory in controlling the problem as treatment in the juveniles stage of the clams.

While other biocidal materials do have some efficacy, e.g., chlorine, chlorophenates and the like, these chemicals are quite persistent and the discharge of waters containing these chemicals back into the receiving stream is subject to regulatory review since each provides its own pollution and/or contamination problems. The present inventors, in reviewing the asiatic clam problem, were attempting to discover a chemical which would not only be effective in controlling the asiatic clams but which would either decompose upon use to less toxic materials and therefore be dischargable to receiving streams without drastically effecting the ecology thereof, or be readily neutralized into relatively safe daughter products. The present inventors found bromonitrostyrene to, in fact, provide all of these properties.

SPECIFIC EMBODIMENTS OF THE INVENTION

Discussion

The following documents the results of an efficacy assessment of Betz ® Slimicide 364 as a mollusk control agent. The target organism of the study was the meroplanktonic juvenile stage of the Asiatic clam *Corbicula fluminea*.

Slimicide 364 is a broad spectrum biocide marketed by Betz Laboratories, Inc. The active biocidal agent of the product is beta-bromo-beta-nitrostyrene (BNS) at a concentration of 10.0% by weight with the remaining 90% being hydrocarbon solvent and stabilizing agents. The product has in the past been registered for use against bacteria and fungi in recirculating cooling water systems only, but due to the natural propensity of the active (BNS) to hydrolyze quickly to less toxic products and the susceptibility of the BNS to detoxification by use of various oxidizing agents (U.S. Pat. No. 3,524,812) the product was considered a likely candidate for approval in once-through cooling water applications where Asiatic clam problems are commonly experienced. For this reason, and because of the product's toxicity to non-microbial aquatic organisms (96 hr. static acute LC 50 range 1-2 ppm product to rainbow trout and bluegill sunfish) Slimicide 364 was examined for its efficacy as a molluscacidal agent against planktonic, entrainable larvae stage Corbicula, the seed plant of hard fouling problems commonly experienced in once-through cooling water systems.

Materials and Methods

Naturally spawned pediveliger larvae were collected from laboratory cultures of adult Corbicula collected from a tributary of the Delaware River, Bucks County, PA (Scientific Collector Permit No. 34, Pennsylvania Fish Commission, 1983). Only spawns released during the 24 hour period immediately preceding individual testing periods were used. The larvae were microscopically examined and confirmed to be in the pediveliger stage: possession of a fully developed foot and a greatly reduced or absent velum. Only larvae exhibiting active foot and shell movements and ciliary activity were retained for testing. The clams were observed under a stereomicroscope using up to 80× magnification. The larvae were not fed following collection from the adult cultures.

Three static acute bioassays were conducted with Slimicide 364. The three tests differed only in the period of toxicant exposure used: 24, 4, and 3 hour exposures. The concentrations of Slimicide 364 examined in each test were 25, 50, 100 and 200 ppm, spanning the application range typically employed in recirculating water systems. Boerner glass microslides were used as the test containers. Four replicate slide cells were used with each test solution. Approximately 10 larvae were micropipetted into each cell containing diluent water for acclimation one day prior to the start of the tests. The test animals were again examined immediately before testing. Only viable individuals were used for toxicant exposure, which usually represented 100% of the animals initially entered for acclimation. The diluent in each cell was removed by micropipetting, leaving only a water film covering the larvae, and immediately replaced with either control diluent or a toxicant solution. Mortality counts were made hourly during the exposure periods except for the 24 hour exposure test where observations were taken at 1, 2, 4 and 24 hours. All mortality counts were corroborated by an independent observer. Mortality was defined as the cessation of all internal body movements or the necrosis of the body tissues. At the end of the respective exposure periods the control and exposure solutions were removed as noted above and replaced with fresh diluent. After a 24 hour recovery period the final enumerations of mortality were made. During testing, the Boerner microslides were stored in airtight plastic trays above a shallow layer of water to prevent evaporation of the test solutions.

The diluent water used in testing and culturing was from a municipal water source which was dechlorinated through activated carbon filtration, heavily aerated, sterilized and autoclaved prior to use. This water is of suitable quality for continuous culture of the Cladoceran species *Daphnia magna* and has been demonstrated capable of sustaining the larval clams throughout the testing periods (100% survival in all control groups - see Table).

ducted and demonstrates efficacious control within the product range 100-200 ppm. This particular test demonstrates appreciable mortality within the first hour of exposure to 100 and 200 ppm concentrations (50% mortality) with continued increases in mortality through the remainder of the exposure period. The test also demonstrates an obvious belated acute toxic response for the higher product concentrations.

The toxicity data generated for Slimicide 364 was considered to represent conservative estimates of efficacy potential against planktonic pediveliger Corbicula larvae due to the use of static bioassay procedures and nominal product concentrations. Unpublished data from Betz Laboratories, Inc. have shown the toxicity decay rate of BNS to be consistent with known chemical degradation rates (Friend and Whitekettle, 1980) with a half-life of initial toxic effects estimated to range 4 - 7 hours from studies with the Cladoceran species *Daphnia magna*. The product exposure periods examined in this study have at the very minimum overlapped this decay period, which theoretically should have a diminutive effect on toxicity estimates generated. The lack of mortality observations during the initial hour of product exposure makes it impossible to interpolate as to what point or to what extent the degradation of the product active has effected the efficacy assessment. It is however anticipated that dynamic product exposure applications would demonstrate a higher level of efficacy.

TABLE

| | Summary of Experimental Data | | | | | | | | | | | | |
|---|---|---|---|---|---|---|---|---|---|---|---|---|---|
| Product | Cumulative Percent Mortality[a] | | | | | | | | | | | | |
| Concentration | 24 Hr. Exposure Test Obvservation Time (Hrs.) | | | | | 4 Hr. Exposure Test Observation Time (Hrs.) | | | | | 3 Hr. Exposure Test Observation Time (Hrs.) | | | |
| (ppm of Slimicide 364) | 1 | 2 | 4 | 24 | 24R[b] | 1 | 2 | 3 | 4 | 24R[b] | 1 | 2 | 3 | 24R[b] |
| 0 | 0 | 0 | 0 | 0 | 0 | 0 | 0 | 0 | 0 | 0 | 0 | 0 | 0 | 0 |
| 25 | 7.5 | 22 | 27 | 43 | 54 | 17 | 20 | 23 | 23 | 28 | 6 | 6 | 6 | 8 |
| 50 | 28 | 36 | 39 | 48 | 54 | 37 | 47 | 52 | 52 | 70 | 35 | 35 | 35 | 52 |
| 100 | 33.5 | 36 | 57 | 81 | 83 | 51 | 68 | 74 | 83 | 94 | 53 | 60 | 68 | 76 |
| 200 | 49 | 58 | 72 | 75 | 78 | 63 | 73 | 78 | 83 | 85 | 51 | 72 | 77 | 90 |

[a]Mortality values given as means of independent replicate counts.
[b]Mortality counts following 24 hours recovery in diluent water.

Results and Discussion

The results of the experimental data are summarized in the following Table. The mortality values presented are percentages of the total number of individuals. Actual mortality Counts did not differ from the mean values presented by more than four percentage units, with the greatest variations occurring in the first hour observations. Apparently, the rate of toxic effect was greatest during this initial exposure interval resulting in minor changes in mortality data between replicate counts. Mortality counts at the later observations periods were highly reproducible.

Slimicide 364 at the concentrations tested produced a graduated dose response effect with greater than 80% mortality achieved in all cases at the highest test concentrations. It is significant to note the complete absence of control mortality throughout the three test series. This demonstrated the species handling and bioassay procedures employed to be acceptable throughout the time frame of each test, suggesting their independence from any observed toxic effects.

The susceptibility of larval clams to short-term product exposures was determined to be promisingly high. The dose response relationship for the three hour exposure test was the most consistent of the three tests con- While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What we claim is:

1. A method for controlling the fouling potential of mollusks in an aqueous system which comprises adding to said system an effective amount for the purpose of an effective nitrostyrene compound.

2. A method according to claim 1 wherein the mollusks are asiatic clams.

3. A method according to claim 2, wherein the aqueous system is the aqueous system of a cooling water system.

4. A method according to claims 1, 2 or 3 wherein the compound is bromonitrostyrene.

5. A method according to claim 4 wherein said compound is beta-bromo-beta-nitrostyrene.

6. A method for controlling the fouling potential of mollusks in an aqueous system which is prone to such which comprises adding to said system a sufficient amount of an effective nitrostyrene compound to substantially destroy the planktonic juveniles of said mollusks.

7. A method according to claim 6 wherein the mollusks are comprised primarily of asiatic clams.

8. A method according to claims 6 or 7 wherein said compound is a bromonitrostyrene compound.

9. A method according to claim 8 wherein said compound is beta-bromo-beta-nitrostyrene.

10. A method of assuring that the flow of water through a cooling water system is not impeded or curtailed due to the growth and proliferation of mollusks without significant attendant contamination of waters discharged from said cooling water system which comprises feeding to the incoming water to said system a sufficient amount of an effective nitrostyrene compound to destroy any planktonic juveniles of said mollusks which may be contained in said incoming water.

11. A method according to claim 10 wherein the mollusk is an asiatic clam.

12. A method according to claim 11 wherein said compound is bromonitrostyrene.

13. A method according to claim 12 wherein the compound is beta-bromo-beta-nitrostyrene.

14. A method according to claim 10, 11, 12 or 13 wherein the aqueous system is the aqueous system of a cooling water system.

* * * * *